United States Patent [19]

Pontis et al.

[11] Patent Number: 5,529,752
[45] Date of Patent: Jun. 25, 1996

[54] ANALYTICAL WORK STATION

[75] Inventors: George Pontis, Palo Alto; Michael Lacy, Ben Lomand; Vladimir Drbal, Belmont; Calvin Chow, Portola Valley; Thomas Smith, Palo Alto; Rick Smethers, Milpitas; Debra A. Ross; Gregory Kirk, both of Redwood City; Jonathan Briggs, Los Altos; Lev Leytes, Palo Alto; Suresh N. Mehta, Pleasanton, all of Calif.

[73] Assignee: Molecular Devices Corporation, Sunnyvale, Calif.

[21] Appl. No.: 361,980

[22] Filed: Dec. 22, 1994

Related U.S. Application Data

[62] Division of Ser. No. 33,169, Mar. 16, 1993, abandoned, which is a division of Ser. No. 297,767, Jan. 17, 1989, Pat. No. 5,252,293.

[51] Int. Cl.⁶ .................................................. G01N 35/10
[52] U.S. Cl. .............................. 422/63; 422/58; 422/81; 422/82.05; 422/100; 422/101; 422/104; 436/43; 436/46; 436/174; 436/177
[58] Field of Search ................................ 422/63, 99, 100, 422/101, 103, 104, 58, 82.05, 82.01, 82.02, 82.03, 81; 436/175, 46, 177, 47, 178, 48, 180, 49, 164, 165, 43, 174; 435/300, 301; 204/403, 222, 400

[56] References Cited

U.S. PATENT DOCUMENTS

| | | |
|---|---|---|
| 3,146,163 | 8/1964 | Brewer . |
| 4,299,916 | 11/1981 | Litman et al. . |
| 4,317,726 | 3/1982 | Shepel ................................. 210/236 |
| 4,366,241 | 12/1982 | Tom et al. . |
| 4,493,815 | 1/1985 | Fernwood et al. .................. 422/101 |
| 4,497,259 | 1/1989 | Matkovich et al. ................ 422/101 |
| 4,704,353 | 11/1987 | Humphries et al. .................... 435/4 |
| 4,758,786 | 7/1988 | Hafeman ........................... 324/158 D |
| 4,777,021 | 10/1988 | Wertz et al. ........................ 422/101 |
| 4,787,988 | 11/1988 | Bertoncini et al. ................ 210/808 |
| 4,834,946 | 5/1989 | Levin .................................. 422/101 |
| 4,849,330 | 7/1989 | Humphries et al. . |
| 4,855,109 | 8/1989 | Muraishi et al. ..................... 422/63 |
| 4,857,272 | 8/1989 | Sugaya .................................. 422/65 |
| 4,911,794 | 3/1990 | Para et al. ........................... 204/1 T |
| 4,915,812 | 4/1990 | Parce et al. ......................... 204/403 |
| 4,934,817 | 7/1990 | Gassenhuber . |
| 4,948,737 | 8/1990 | Quenin et al. . |
| 4,960,691 | 10/1990 | Gordon et al. . |
| 4,960,692 | 10/1990 | Lentrichia et al. . |
| 5,037,613 | 8/1991 | Shaw et al. ........................... 422/64 |
| 5,039,493 | 8/1991 | Oprandy ............................. 422/101 |
| 5,049,359 | 9/1991 | Azuma et al. ........................ 422/67 |
| 5,075,079 | 12/1991 | Kerr et al. ............................ 422/64 |
| 5,281,395 | 1/1994 | Marbart et al. ................... 422/82.05 |

FOREIGN PATENT DOCUMENTS

WO8804428  6/1988  WIPO .

Primary Examiner—Jill Warden
Assistant Examiner—Long V. Le
Attorney, Agent, or Firm—Banner & Allegretti, Ltd.

[57] ABSTRACT

This invention encompasses a work station for conducting assays which comprises filtering assembly, a slide reading assembly, and a slide with a porous filter membrane wherein the slide has a means for aligning the slide within the filter assembly to filter reagents on predetermined portions of the porous filter membrane and also to position the slide in the slide reading assembly so that detection will occur in those same predetermined locations.

15 Claims, 7 Drawing Sheets

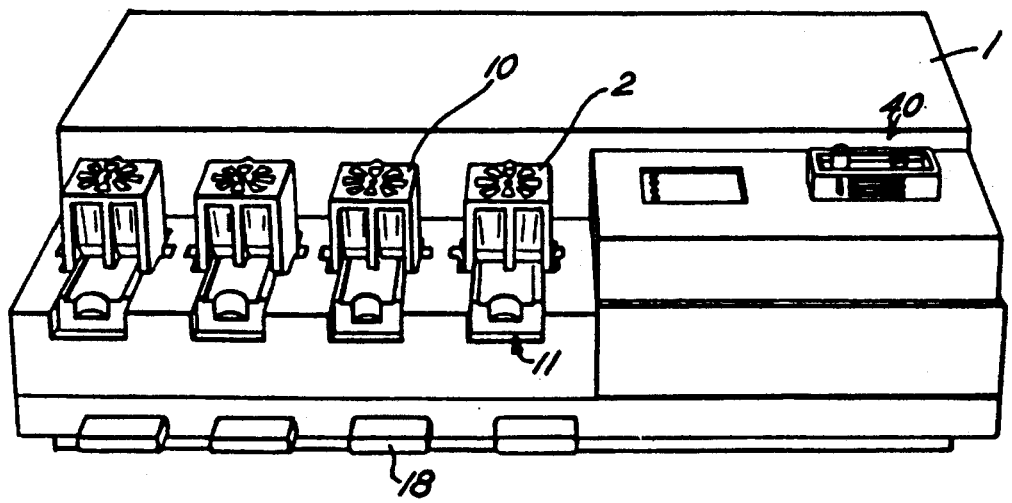
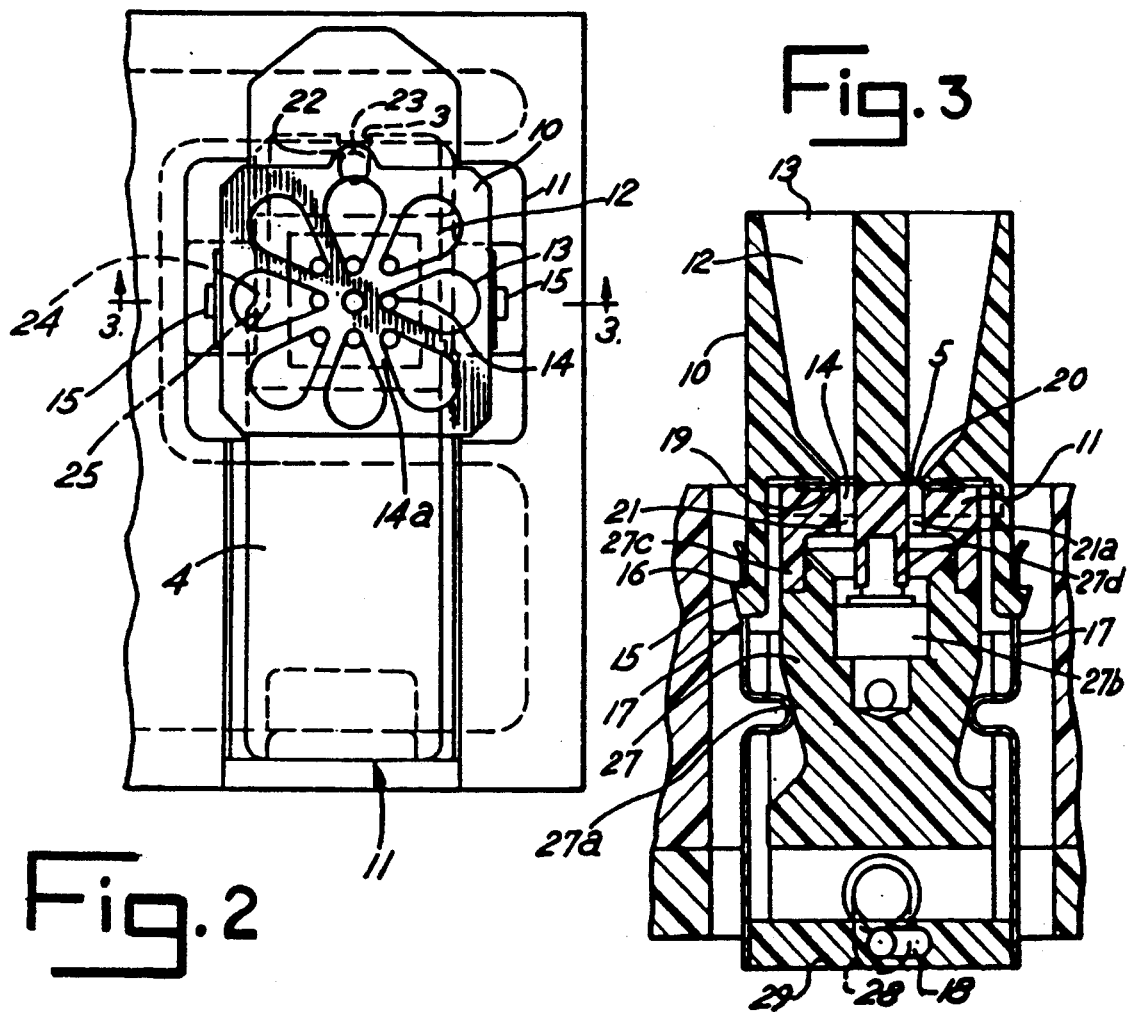

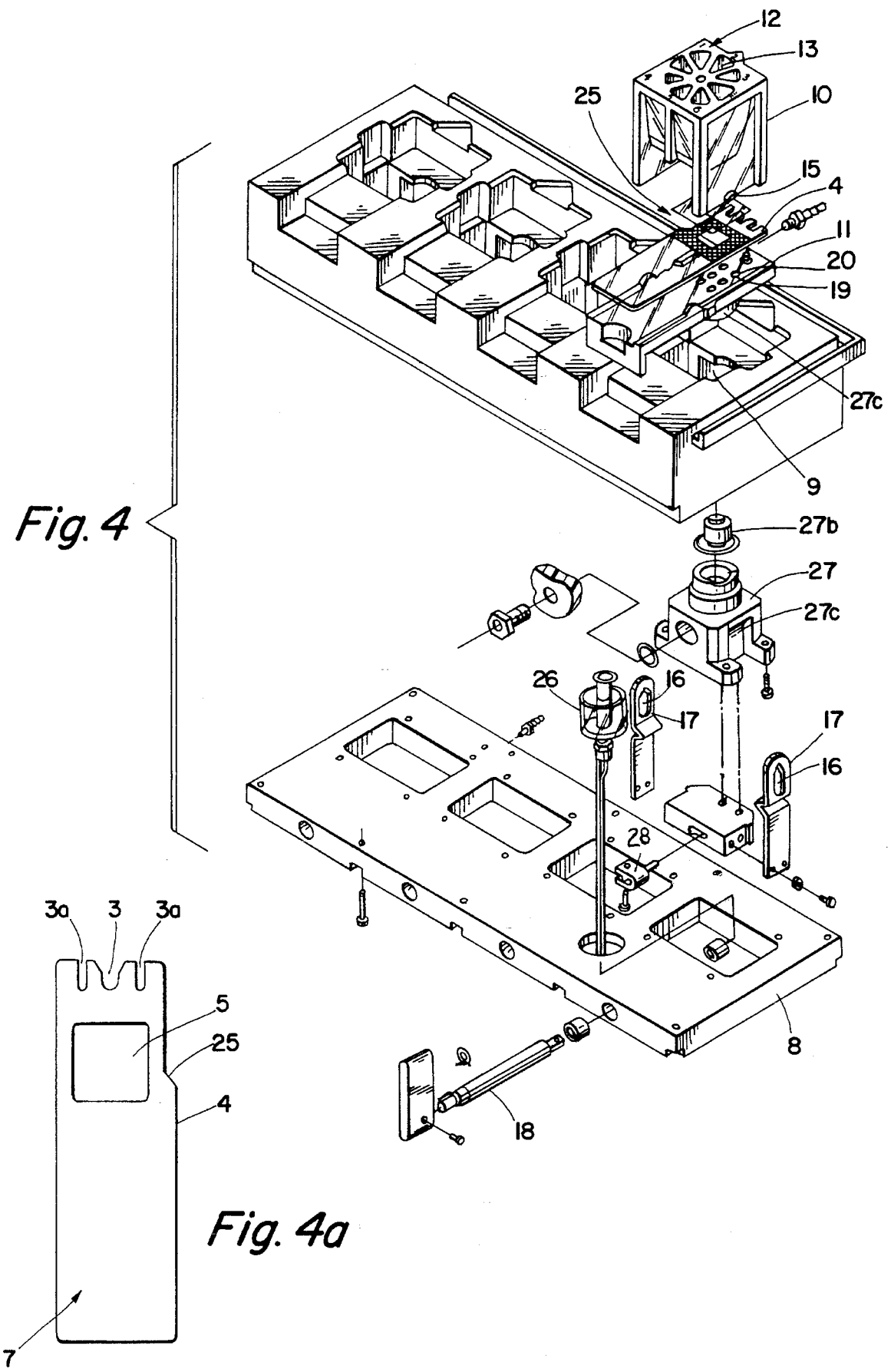

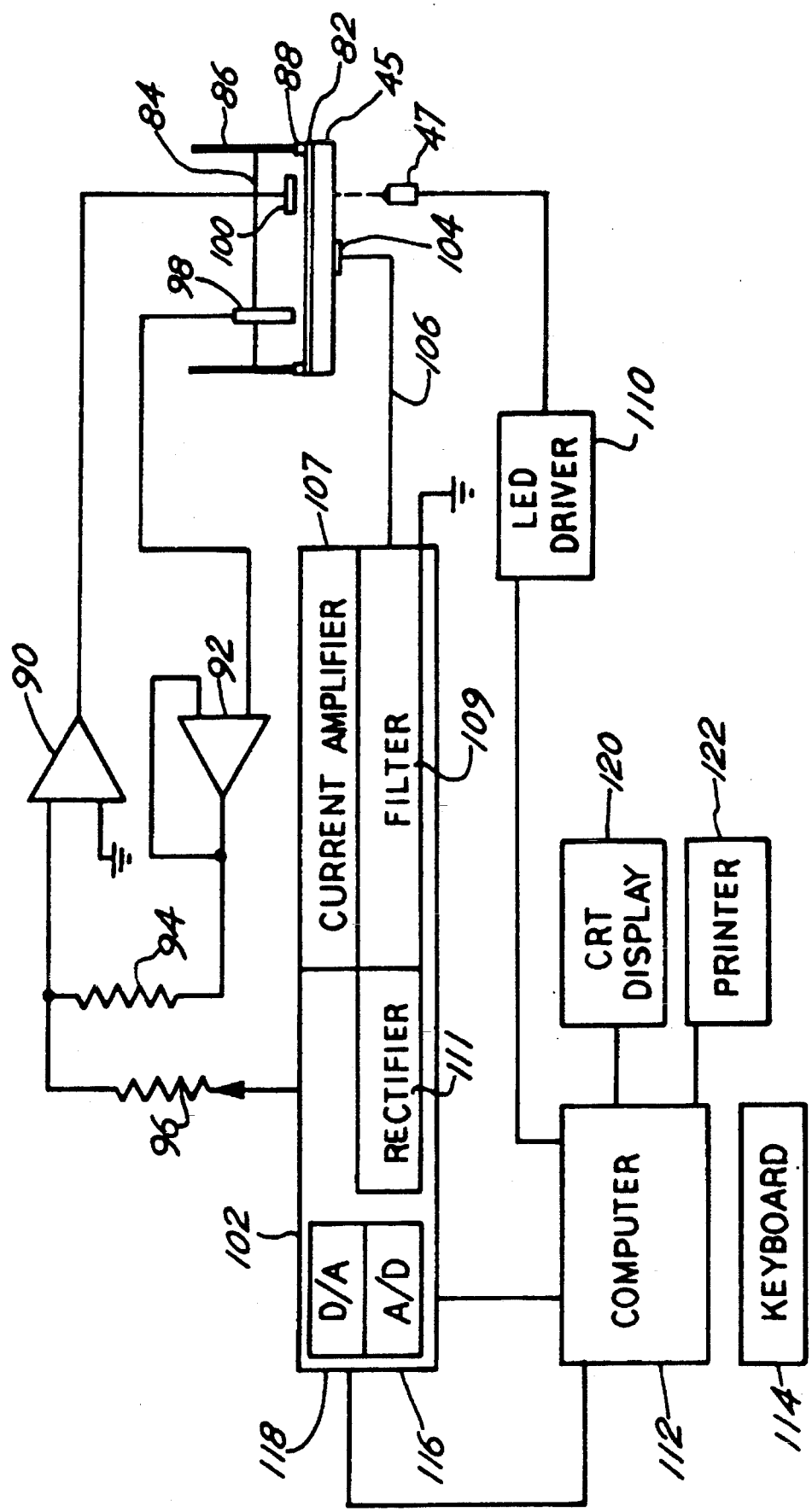

ANALYTICAL WORK STATION

RELATED APPLICATIONS

This is a division of application Ser. No. 07/033,169, filed Mar. 16, 1993, now abandoned, which is a division of application Ser. No. 07/297,767 filed Jan. 17, 1989, now U.S. Pat. No. 5,252,293.

BACKGROUND OF THE INVENTION

1. Field of the Invention

This invention relates to the field of analytical devices where analytes are filtered and bound to a membrane and the membrane is then analyzed for the presence of analyte.

2. Description of the Prior Art

The prior art describes a wide variety of filtering devices ranging from filter paper to individual test units which involve binding specific binding substances such as antibodies and antigens to porous filter membranes as described in U.S. Pat. No. 4,642,285. U.S. Pat. Nos. 4,703,353; 4,591,550; 4,758,786 and 4,704,353 and references therein disclose a photoresponsive electrode generally adaptable to measurements made in the present invention. U.S. Ser. No. 065,418 filed Jun. 18, 1987 assigned to the same assignee as this application discloses a Zero Volume Electrochemical Cell where analytes on porous filter membranes are measured by means of a photoresponsive electrode. U.S. Ser. No. 258,894 assigned to the same assignee as this invention, is directed to Hapten Derivatized Capture Membranes useful as membranes for the slides of this invention.

References of interest include U.S. Pat. Nos. 4,020,830 to Jense, et al.; 3,975,238 to Bean, et al.; 4,238,757 to Schenck; 4,486,272 to Fujihira, 4,293,310 to Weber; and 4,444,892 to Malmros; and International Patent Publications Nos. WO83/02669 and WO85/04018. See also *"Experimental Electrochemistry for Electrochemists,"* Sawyer and Roberts, Wiley-Interscience, pp. 350–353.

U.S. patents of interest also include U.S. Pat. Nos. 4,168,146, which concerns a test strip for immunoassays, where the extend to which an analyte travels is related to the amount of analyte in the medium; 4,298,688, which involves a three-zone strip, where the extent of travel of an enzymatic product is determinative of the amount of glucose analyte; 4,299,916, which concerns an assay technique employing a support for detection of the analyte; 4,361,537, which employs strips in conjunction with RIAs; 4,366,241, which concerns employing a small test zone for concentrating a particular component of the assay medium in a small area; 4,435,504, which concerns an immunochromatograph employing channeling; 4,442,204, which concerns using homogeneous assay reagents on solid support where displacement of labeled conjugate-analyte complex by analyte provides the desired signal; 4,533,629, which employs a simultaneous calibration technique for heterogenous immunoassays; 4,446,232, which employs a solid support having a zone occupied by labeled conjugate, followed by receptor, where binding of analyte to the labeled conjugate allows the labeled conjugate to traverse the receptor zone to a detection zone; 4,447,526, which employs a homogenous specific bonding assay system in conjunction with carrier matrix; and 4,454,094, which involves displaced apart layers through which a medium traverses, where reagent from one layer diffuses to the other layer in relation to the amount of analyte in the medium.

BRIEF DESCRIPTION OF THE DRAWINGS

FIG. 1 Perspective view of the analytical work station.

FIG. 2 Top view of filter assembly.

FIG. 3 Cross sectional 3-1 view of FIG. 2.

FIG. 4 Disassembled filter assembly.

FIG. 4a Top view of the slide.

FIG. 8 Schematic diagram of circuit.

SUMMARY OF THE INVENTION

Figure 5:
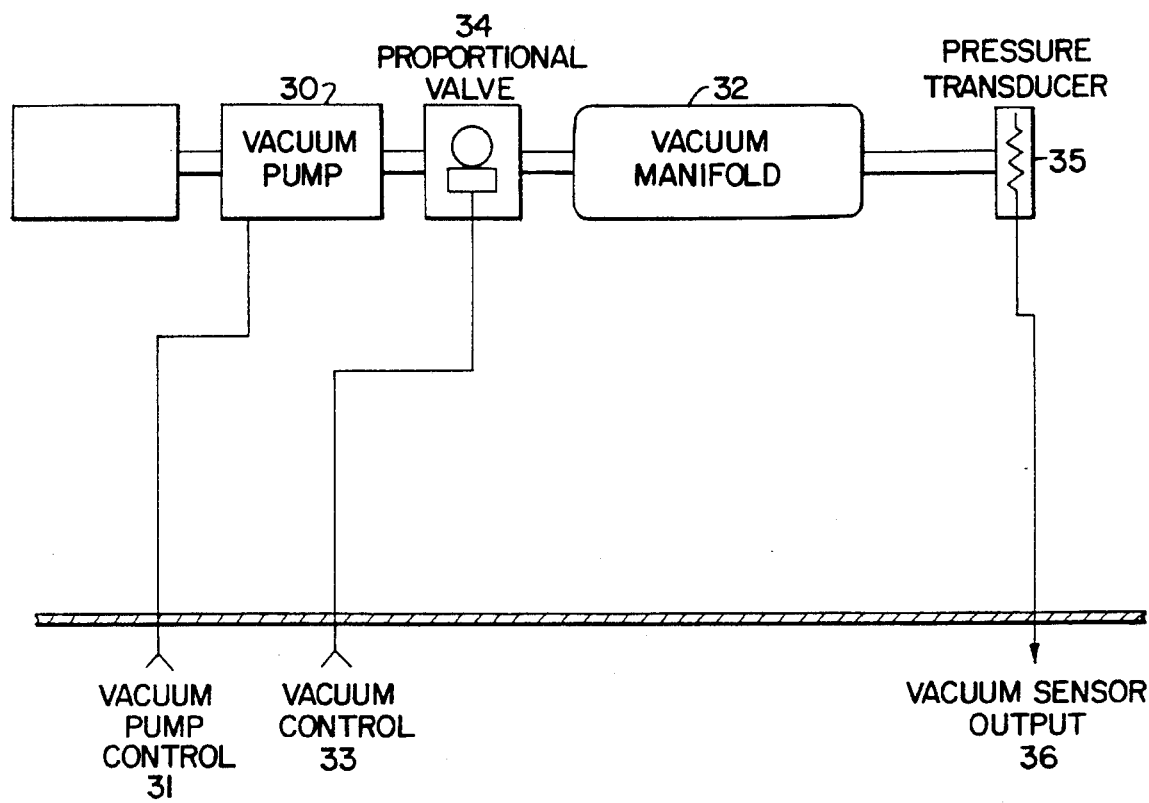
FIG. 5 Schematic of the vacuum system.

This invention encompasses a work station for conducting assays which comprise a filtering assembly, a slide reading assembly, and a slide with a porous filter membrane wherein the slide has a means for aligning the slide within the filter assembly to filter an analyte or analyte complex at a plurality of predetermined locations on the porous filter membrane and also to position the slide in the slide reading assembly so that detection will occur in those same predetermined locations.

This invention encompasses an analytical work station which has a filtering assembly, a slide with a porous filter membrane and a slide reading assembly.

The filtering assembly comprises a combination of:

1. a block with a top and bottom surface, the block having a plurality of channels with inlet ports on the top surface and exit ports on the bottom surface and a first alignment means;
2. a vacuum plate having an upper and lower surface wherein the lower surface has a vacuum fitting defining an area on the lower surface, with a plurality of vacuum ports from the upper to lower surface within the area defined by the vacuum fitting, the vacuum plate having a second alignment means;
3. a slide defining an opening which is covered by a porous filter membrane and further having a third alignment means.

The block and the vacuum plate fit together to form a space for removably inserting the slide between the bottom surface of the block and the upper surface of the vacuum plate and the first, second, and third alignment means align the block, vacuum plate, and slide such that the exit ports of the block, porous filter membrane, and vacuum ports are aligned so that when a vacuum is applied through the vacuum fitting, liquids in the block channels separately flow through the exit ports, through the porous filter membrane, and through the vacuum ports so that liquids from one channel do not mix with liquids from other channels on the porous filter membrane. The analytes or analyte complexes in the filtered liquid are fixed on the porous filter membrane in a predetermined location so as to substantially concentrate the analyte or complexes of the analyte.

The slide is a thin flat generally rectangular plastic sheet with a front and rear end. The front end of the slide has a notch as a means for aligning the slide both in a filter assembly and a reading assembly. The rear end of the slide has an area for manually grasping the slide. The front, approximately a third of the slide, defines an opening which is covered with a porous filter membrane. A section of the front one third of the slide is narrower than the rear section of the slide. The narrower section also serves as a means for aligning the slide in both a filtering assembly and the slide reading assembly. The alignment means provide for filtration of analyte onto predetermined locations on the porous filter membrane in the filter assembly and for detection of analyte at these same predetermined locations in the slide reading assembly. The porous filter membrane has a specific binding substance such as a hapten, for example, biotin so that the porous filter membrane can capture a specifically binding analyte complex at a specific location on the filter membrane. For example, an avidin or streptavidin complex is used in conjunction with a biotin labeled membrane.

The slide reading assembly has a housing with a top, bottom, and inner and outer sidewall sections. The inner side wall section has at least one window or a plurality of holes as windows with a photoresponsive electrode mounted above the windows on the inside of the inner wall section so that light from an external source can pass through the holes to the external surface photoresponsive electrode.

The top section of the housing has an opening for receiving a slide to be analyzed. The slide has a porous filter membrane with analyte or analyte complexes to be determined at predetermined locations on the porous filter. The housing has a means for aligning, the analyte-containing region of the porous filter membrane on the internal surface of the photoresponsive electrode opposite the holes in the housing which allow light to pass to the photoresponsive electrode.

A resilient plunger is mounted in the outer side wall section of the housing opposite the photoresponsive electrode. The plunger has a stem and pad which is pivotally mounted on the stem and located within the housing such that when the plunger stem is externally pushed into the housing by a stepping motor the pad compresses the porous membrane against the inner surface of the photoresponsive electrode. This reduces electrolyte volume and improves sensitivity.

There is a liquid chamber within the housing with exit and entrance ports for liquids located in the top section of the housing. The inner surface of the photoresponsive electrode is within the liquid chamber and exposed to the liquid. The porous filter membrane is aligned above the inner surface of the photoresponsive electrode also in the liquid chamber.

There is a light source comprising an array of light emitting diodes (LEDs) for independently irradiating portions of the photoresponsive electrodes with intensity modulated light through the holes in the housing. The area of the photoresponsive electrode exposed to intensity modulated light is opposite the area of the porous filter membrane having filtered analyte or analyte complex.

There is also an electrical means for measuring the rate of surface potential change of those portions of the photoresponsive electrode which are exposed to the intensity-modulated beam of light through the holes in the housing. A chemical reaction which alters the surface potential is occurring between the analyte or analyte complex on the porous filter membrane and a reagent in the liquid in the liquid chamber so as to change the surface potential of an exposed portion of the photoresponsive electrode. The electrical means includes a counter electrode or reference electrode and a control electrode, an operation amplifier, and a computer for processing the signal data.

Thus, in operation a reaction between specific binding substances is conducted in a test tube, for example, the reaction between DNA, enzyme labeled anti-DNA, SS-binding protein bound to a biotin, and avidin or streptavidin. This complex is filtered through a biotinylated porous filter membrane such that the (enzyme containing) analyte complex is captured by the porous filter membrane in small spots at a predetermined location on the membrane. The locations of these spots are fixed by the alignment means in the block, slide, and vacuum plate. The slide is removed from the filter assembly and placed in the slide reading assembly which contains a substrate to the enzyme in the liquid in the liquid chamber. The plunger is pushed in by a stepping motor to press the pad of the plunger against a photoresponsive electrode. This decrease in volume increases sensitivity by decreasing the amount of pH buffer in the measurement volume. The alignment means in the reading assembly aligns the enzyme-containing spots of the porous filter membrane opposite the holes for light in the housing. The reaction of enzyme and enzyme substrate results in a change in surface potential in the local area of the photoresponsive electrode which is measured by the above electrical means in conjunction with the action of the intensity-modulated light on the photosensitive electrode.

Thus, the filter assembly provides for concentrating a complex containing the analyte to be determined in a small area of a porous filter membrane which is predetermined by the alignment means. This predetermined location of the spots on the filter membrane can then be aligned with a specific reading location in the slide reading assembly by complimentary alignment means. The pad which compresses the porous filter membrane against the photoresponsive electrode uniformly reduces volume and increase sensitivity. In this way picogram (pg) quantities of analyte such as DNA can readily be determined. The filter and slide reading assemblies provide for filtering and reading of standards, controls and unknowns under similar conditions as well as for the ease of identification of the sample, and for obtaining an analytical result from the same sample.

DETAILED DESCRIPTION OF THE INVENTION

The Slide

FIG. 4a is a top view of the slide.

The slide 4a is made of a thin plastic sheet and has an opening which is covered with a porous filter membrane 5. The notch 3 at the front end of the slide and the angle 25 defined by the narrow and wide portion of the slide serve as means for aligning the slide in the filter assembly and the slide reading assembly. Slits 3a permit the notch to resiliently expand. The rear end of the slide has an area 7 for manually grasping the slide. A porous filter membrane suitable for practicing this invention is described in great detail in Ser. No. 258,894 assigned to the same assignee of this application. Ser. No. 258,894 is incorporated herein by reference.

The porous filter membrane is capable of filtering from a solution containing a specifically binding complex having an anti-hapten bound to a binding member of the specifically binding complex.

The material of the porous filter membrane is selected from material to which protein or other macromolecule can be adhered. A variety of materials may be used. Those skilled in the art will appreciate that porous membranes made of nylon, cellulose acetate, polyolefin, polyacrylamide, nitrocellulose or other porous materials may be employed in the present invention. Other synthetic or naturally occurring materials which will adhere a protein or other macromolecule may also be used. A preferred membrane is made from nitrocellulose. Physical characteristics of the porous filter membrane in the slide are:
(a) pore size:0.25 to 12.0 μm
(b) thickness:50 to 180 μm
(c) bubble point:75 to 6 psi
A membrane having 1–10 m mol (per liter of compressed membrane volume) buffering capacity is preferred.

Haptens are substances which do not elicit antibody formation unless complexed to macromolecules and which may be employed as specific organic materials for which specific binding substances can be provided. Antibodies to haptens can be formed by binding the hapten to a protein so as to elicit an antibody response. A specific binding substance is any substance or group of substances having a specific binding affinity for the hapten to the exclusion of other substances. The hapten must be able to bind to a protein or other macro-molecule directly or through an extended linking group. Examples of haptens which may be used include steroids such as estrone, estradiol, testosterone, pregnanediol and progesterone; vitamins such as $B_{12}$, biotin and folic acid; triiodothyronine, thyroxine, histamine, serotonin, digoxin, prostaglandins, adrenalin, noradrenalin, morphine, vegetable hormones and antibiotics such as penicillin.

When the hapten is a substance having a naturally occurring receptor, the receptor can be utilized as the anti-hapten provided the receptor can be isolated in a form specific for the hapten. Illustrative haptens which have naturally occurring receptors include thyroxine, many steroids, polypeptides, such as insulin, angiotensin, biotin and many others. Receptors for this class of haptens are usually proteins or nucleic acids.

Extended linking groups are groups that will bind the hapten to the protein or macro-molecule in such a way that the hapten has better access to the anti-hapten. Where an extended linking group is not needed, a hapten, such as biotin without an extended linking group, is bound to a functional groups on a membrane or to a function group on a protein which can be disbursed on the membrane.

Preferentially the extended linking group having an hapten bound to one end will be bound to the protein or macro-molecule with an amide bond; the amine of the amide bond arising from the protein and the carboxyl of the amide bond arising from the carboxy terminus of the extender group. Free carboxyl or hydroxyl groups on proteins can likewise be used.

The proteins used as carriers include, but are not limited to, bovin serum albumin (BSA), bovine gamma globulin, and fibrinogen. A preferred membrane for use with the slide has 5–20 molecules of biotin bound to bovine serum albumin (BSA). The BSA is further adhered to the surface of the membrane. The preferred linking group is the following:

Complexes typically removed from solution by the membrane include:

| Porous Filter Membrane | Complex |
| --- | --- |
| membrane - hapten | anti hapten-Ab Ag-Ab (enzyme) |
| membrane - (biotin) | (streptavidin)-Ab' Ag' Ab (enzyme) |

The antibodies employed may be either polyclonal or monoclonal antibodies and are produced in response to the target antigen of the assay. Methods for the production of antibodies to various biological substances are well known in the art.

The antigens targeted by the assay include, but are not limited to antigens such as IgE, prostatic acid phosphatase, prostate specific antigen, alphafetoprotein, carcinoembryonic antigen, leutenizing hormone, creatine kinase MB, Human Chorionic Gonadotropin (HCG) and other antigens in serum, plasma, urine, or other liquid media.

Polydeoxyribonucleotides can be determined by reactions with single strand DNA binding protein (SSB) and anti-DNA antibodies. Thus, various combinations of labeled SSB or anti-DNA and biotinylated SSB or anti-DNA are employed. In this embodiment streptavidin is bound to the biotinylated SSB or anti-DNA so that the complex can be bound to the capture membrane having biotin. The article in *Biochemistry*, 25:21 (1986) describes the large scale over production of single-strand binding protein (SSB) from E. coli. Monoclonal antibodies to DNA have been used to measure DNA in biological fluids, *Journal of Immunological Methods*, 88, (1986) 185–192.

This complex and membrane can be viewed as follows:

| Porous Filter Membrane | Complex |
| --- | --- |
| membrane - biotin | streptavidin-biotin-anti-DNA/DNA-SSB-enzyme |

Examples of enzymes which may conveniently be employed are, malate dehydrogenase, lipase, delta-5-keto-steroid isomerase, yeast alcohol dehydrogenase, yeast glucose-6-phosphate dehydrogenase, alpha glycerophosphate dehydrogenase, triose phosphate isomerase, horseradish peroxidase, alkaline phosphatase, asparaginase, glucose oxidase, beta-galactosidase, and more preferably, urease. Normally, it is preferred that the enzyme be in a pure form, free of contaminating proteins.

The preparation of the enzyme-labelled biological substances can be accomplished in various ways known in the art. Examples of the coupling of biological substances to enzymes are described in, for example, L. A. Steinberger, Immunocytochemistry, Prentice Hall, N.J. (1974).

The enzyme label on porous filter membrane is made to react with an enzyme substrate and the extent of reaction is measured by the photoresponsive electrodes and methods described in U.S. Pat. Nos. 4,591,550, 4,704,353, and U.S.

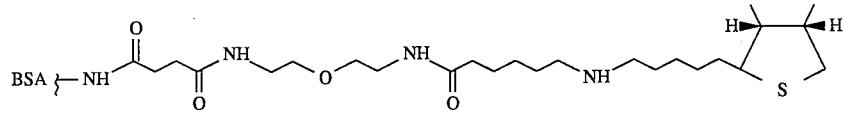

patent application Ser. No. 876,925, filed Jun. 20, 1986 and assigned to the same assignee as this application. The slide reading assembly is an adaptin and improvement of these devices to read the predetermined locations on the membrane where the enzyme has been filtered.

The photoresponsive electrode can be influenced by a wide variety of redox systems where the redox reaction occurs at the surface of the photoresponsive electrode where the light strikes the surface of the photoresponsive electrode.

The Filter Assembly

FIG. 1 is a perspective view of the analytical work station 1. In this embodiment there are four filter assemblies 2 and a slide reading assembly 40. FIG. 2 is a top view of a filter assembly which shows a filter block 10, vacuum plate 11 and slide 4 and FIG. 3 is a cross-sectional view of 3—3 of FIG. 2. The filter block 10 has a plurality of channels 12 which narrow from the inlet port 13 to the exit port 14. The exit ports 14 are centrally located in a smooth surface area 14a at the bottom end of the block. The bottom surface of the block has a hole 23 as an alignment means to align the slide with the vacuum plate 11. The block has small projections 15 at the lower end of the side walls which are gripped by the clamping mechanism spring clip 17 through opening 16 to fix and release the slide between the filter block 10 and the vacuum plate 11 by turning lever 18 as shown in FIGS. 1 and 3.

The vacuum plate 11 has on its upper surface a plurality of radial cylinders 19 through which pass the vacuum ports 20 as shown in FIG. 3 which is a cross-section of 3—3 of FIG. 2, also see FIG. 4. The smooth lower surface of the filter block and the smooth upper surface of the raised cylinders of the vacuum plate compress the membrane 5. When the lever 18 is turned the rotation of the lever moves the spring block 29 up and down as the cam 28 mounted on the lever shaft rotates 90 degrees. The spring clips 17 follow a cam surface 27a and spread in the upper position allowing an easy removal of the filter assembly from the vacuum. In the lower position the spring clips are closed firmly and without any side forces hold the filter block locked against the vacuum plate. This compression prevents fluid from one filter pathway 21 crossing over to another filter pathway 21a. The vacuum plate has a peg 22 which interacts with the hole 23 of the block and the notch 3 of the slide (shown in FIG. 4a) to align the exit ports 14 in the block and the vacuum ports 20 in the vacuum plate. Slits 3a provide for expanding the notch 3 to resiliently clamp the peg 22. The vacuum plate further has a depression 24 which fits the shape of the slide 25 to rigidly fix the slide in place as shown in FIG. 2. Turning 18 in FIGS. 3 and 4 releases the pressure exerted by block 10, and thus permits the slide 4 to be removed from the filtering assembly.

FIG. 4 shows the filter assembly disassembled into its component parts and further illustrates the arrangement of the block 10, manifold bottom 8, slide 4, and vacuum plate 11 as they sit in the vacuum manifold 9. Further illustrated in FIG. 4 are the liquid level sensor 26, manifold insert 27, and check valve 27b which engages vacuum fitting 27c on the vacuum plate 11. FIG. 4 further illustrates how lever 18 interacts with cam 28 and spring block 29 to spring clip 17 which has hole 16 engaged with projection 15 of the filter block 10. Thus turning 18 lowers the block 10 and releases the porous filter membrane 5.

FIG. 3 illustrates the interaction of clamping mechanism 18, 28, 29, 17, 16 and further shows the engagement of spring clip 17 with the manifold insert 27 at point 27a. The manifold insert 27 engages the vacuum plate 11 at the vacuum fitting 27c. The vacuum ports 20 lie within the vacuum fitting 27c and the check valve 27b lies within the manifold insert 27. Projections 27d push against the check valve 27b to open the check valve.

The vacuum system is schematically illustrated in FIG. 5. The vacuum pump 30 is controlled by the vacuum pump control 31. The vacuum to the vacuum manifold 32 is controlled by the vacuum control 33 which operates a proportional valve 34. A pressure transducer 35 provides for the vacuum sensor output 36.

The vacuum manifold serves as an effluent reservoir and as a vacuum reservoir. The individual filter assembly receptacle 9 in the manifold has a manifold insert with a check valve 27b, which is activated with the insertion of the filter base to start the vacuum flow. The liquid level sensor 26 determines when the manifold should be emptied of waste fluid.

The vacuum system provides vacuum to pull solutions in the channels of the filter block through the porous filter membrane on the slide by way of the vacuum ports.

The Slide Reading Assembly

Figure 7:
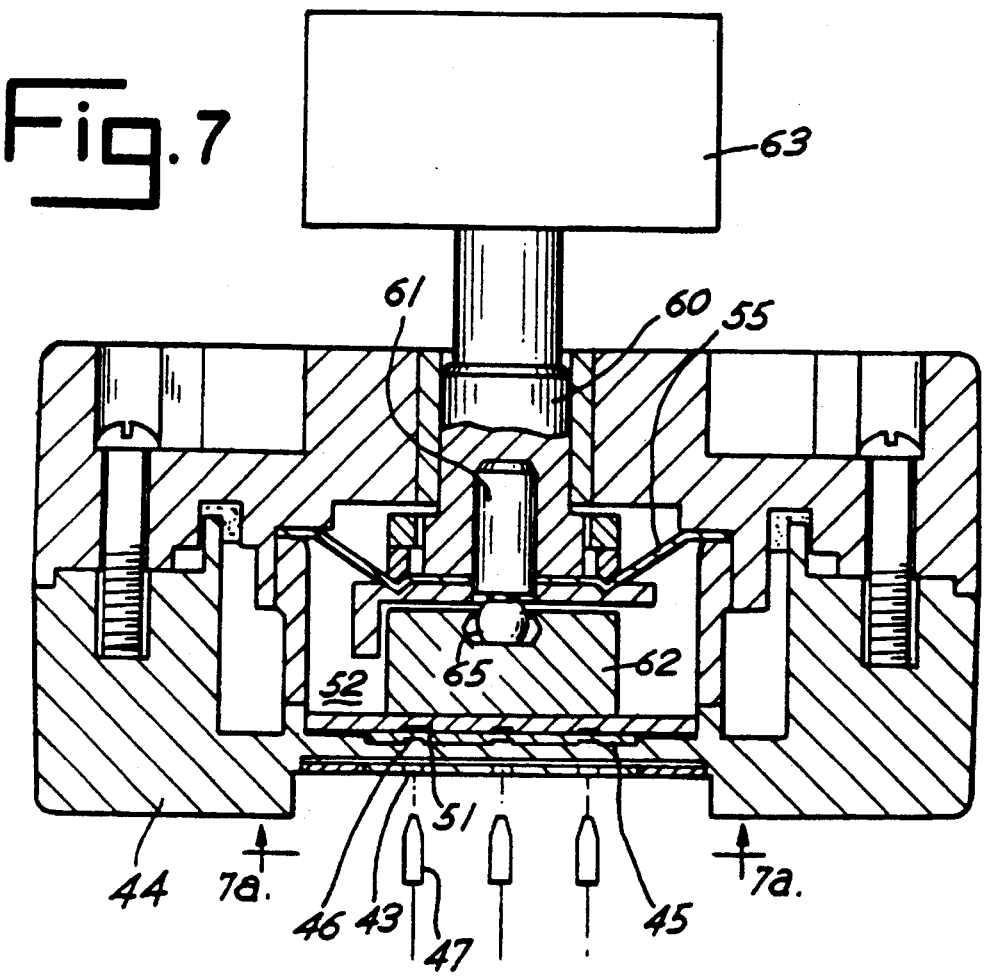
FIG. 7 Cross-section of the filter assembly.
Figure 7A:
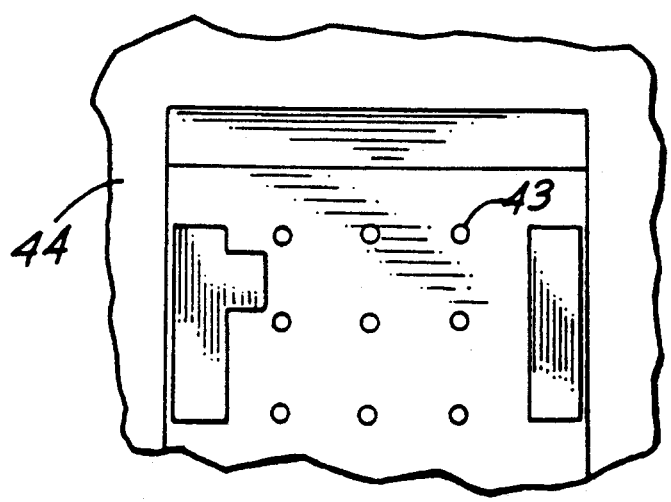
FIG. 7a Holes in inner wall section of housing.

The slide reading assembly is illustrated in FIGS. 6, 6a, 7 and 7a. The housing 40 has a slow 41 in the top end 42 for inserting the slide 4. The housing has an area with a plurality of holes 43 or windows in the inner wall section 44 (see FIG. 7a) and a photoresponsive electrode 45 mounted over the holes. This photoresponsive electrode 45 has a transparent layer of silicon dioxide which defines areas of transparent circular spots 46 which are aligned with the holes 43 in the housing. The windows 43 in the housing and transparent circular spots 46 permit light to pass from the array of LED's 47 from outside the housing to the surface of the photoresponsive electrode as shown in FIGS. 7 and 7a. Within the reading assembly housing is a peg 48 which serves as a means for aligning the slide by engaging the notch 3 (see FIG. 4a) in the front end of the slide. Also there is a depression 49 on a slide support member 50 which further aligns the slide so that the porous filter membrane 5 (see FIG. 4a) is located above the photoresponsive electrode 45 and also the predetermined areas in the porous filter membrane 51 where analytes or analyte complexes are located are aligned above the transparent circular spots 46 on the photoresponsive electrode. The housing also defines a liquid chamber 52 and there is an exit 53 and an entrance port 54 for filling and emptying to liquid chamber 52. The liquid in the liquid chamber is in contact with the photoresponsive electrode and the porous filter membrane. The liquid serves as an electrolyte and contains a reagent that reacts with the analyte or analyte complex on the porous filter membrane. For example, if the analyte complex contains an enzyme, the liquid in the liquid chamber will contain an enzyme substrate and this enzyme/enzyme substrate reaction causes a local change in pH on the surface of the photoresponsive electrode. As shown in FIG. 7 the slide reading assembly has a plunger 60 resiliently mounted by flexing member 55 in the top of the housing. The plunger 60 has a stem 61 and a pivotally mounted pad 62. The ball and socket mounting 65 gives flexibility to the mounted pad 62.

FIG. 7 shows light from LED 47 passing through holes 43 in the inner wall 44 and through the transparent spots 46 on the photoresponsive electrode 45 which are aligned with the predetermined areas 51 in the porous filter membrane 5 where analytes or analyte complexes are located.

This pivotally mounted pad 62 is pushed against the porous filter membrane 5 by a stepping motor 63 which is operatively associated with the stem 61 of the plunger 60. This pad 62 reduces the volume of liquid above the porous filter membrane and greatly increases the sensitivity of the photoresponsive electrode. FIG. 7a illustrates the holes 43 in the inner wall section 44.

U.S. Ser. No. 065,418 filed Jun. 18, 1987 and assigned to the same assignee as this application describes in great detail the photoresponsive electrode and the increase in sensitivity resulting from reducing the volume of liquid above the membrane. The specification of U.S. Ser. No. 065,418 is incorporated herein by reference. The present invention differs from the invention described in U.S. Ser. No. 065,418 in that the slide is aligned so that spots on the membrane having analyte or analyte complex are aligned above the irradiated portion of the photoresponsive electrode and the pivotally mounted pad uniformly compresses the areas of the porous filter membrane where the analyte is located to exclude excess volume of buffering electrolyte so as the greatly increase sensitivity of the photoresponsive electrode for measuring potential changes resulting from the reaction of enzyme substrate and enzyme bound to the porous filter membrane due to the presence of analyte or analyte complex.

The operation of the photoresponsive electrode, including the reference electrode controlling electrode, materials for the electrode, light source, nature of measurable chemical reactions, signal amplification and measurement, types of measurable enzyme and redox reactions and the like are described in great detail in U.S. Pat. Nos. 4,704,353; 4,758,786 and 4,591,550, which are incorporated here by reference. A schematic of an electrical circuit usable in the present invention is shown in U.S. Pat. No. 4,758,786.

FIG. 8 shows a preferred circuit for use with this invention. Shown in FIG. 8 is a schematic diagram of a computer-controlled electronic circuit which may be used to operate the potentiometric reading device in accordance with the present invention. A photoresponsive electrode 45 (e.g. n-type 10–25 ohm-cm, 100 crystalline silicon) polished on one side is covered on the polished side with an insulator 82 which is in contact with an electrolyte 84 enclosed by a chamber wall 86 sealed to the insulator surface by a silicon polymer 88. Operational amplifiers 90 and 92, together with resistors 94 and 96, reference electrode 98, controlling electrode 100, and digital-to-analog converter (D/A) 118 mounted on master circuit board 102, function to determine the potential of the electrolyte with respect to the bulk of the photoresponsive electrode 45. Computer 112, having keyboard 114, varies the potential of electrolyte 84 via the output of D/A 118. The potential of the photoresponsive electrode 45 is held constant at virtual ground by copper lead 106 which is attached to the underside of the photoresponsive electrode 45 through a brass spring and ohmic contact 104. Ohmic contact 104 is made by evaporation of 99% gold—1% arsenic onto the non-insulated silicon surface followed by alloying above the gold-silicon eutectic temperature. One light-emitting diode (LED) 47 of an array of nine similar LEDs (not shown) is powered by LED driver 110 so as to irradiate the photoresponsive electrode at the desired X-Y-coordinate with light of 50% duty cycle, on/off-modulated intensity. Any one of the nine similar LEDs may be selected for light intensity modulation by computer 112 which acts on a switching circuit in LED driver 110. The frequency of intensity-modulation is determined by LED driver 110 to be about 10 KHz. Current-to-voltage converter 107, connected through lead 106, measures the alternating photocurrent generated in photoresponsive electrode 45. The voltage output of current-to-voltage converter 107, is filtered by bandpass filter 109 and rectified by rectifier 111 to give a dc voltage output that is proportional to the alternating current amplitude. This analog dc voltage output is converted into digital form by analog-to-digital converter (A/D) 116 and stored as data in the memory of computer 112. Experimentally-acquired data may be viewed on CRT display 120 and permanently displayed by printer 122.

Figure 9:
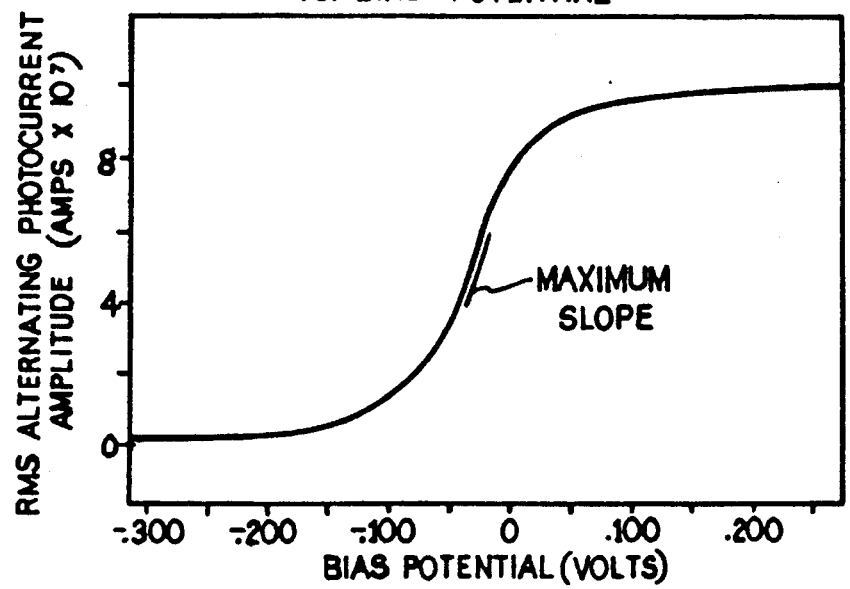
FIG. 9 Alternating current response curve.
Figure 9A:
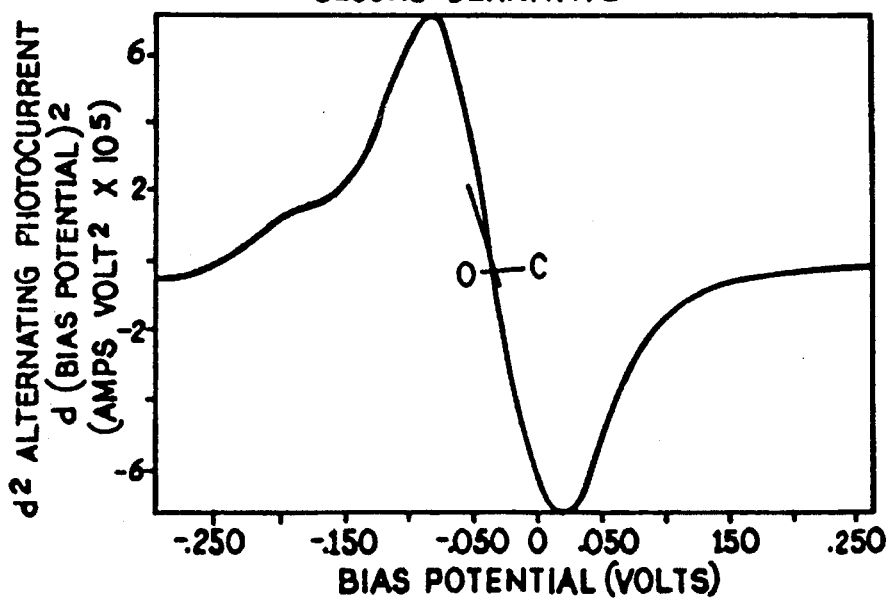
FIG. 9a First derivative of the curve of FIG. 9.

In operation, modulated current is applied from LED driver 110 to cause LED 47 to be modulated in intensity. The output of D/A 118 is ramped by a program in computer 112 so as to ramp the potential of electrolyte 84. The electrolyte potential, in turn, affects the electrical field within the photoresponsive electrode which, in turn, affects the alternating current generated in the illuminated portion of photoresponsive electrode 45, flowing through lead 106, and measured by current-to-voltage converter 107. FIG. 9 shows a typical alternating current response to changes in the electrolyte potential is determined. The values of current vs. electrolyte potential are stored for subsequent analysis of the rate of change in this relationship. In a preferred embodiment of this invention, the point of maximum slope in the curve of FIG. 9 is determined, i.e. that point at which the resulting alternating photocurrent finds its maximum changes for a given change in electrolyte potential. A convenient way of determining this point of maximum slope of the photocurrent of FIG. 9 is to take the second derivative and determine where the second derivative is equal to zero. This is depicted in the graph of FIG. 9a. To avoid consideration of the data points where the alternating photocurrent is varying only slightly vs. electrolyte potential, the date near the maximum or minimum alternating photocurrents are not used in the analysis. For example, the data points associated with photocurrent less than 10% and more than 90% of the maximum alternating photocurrent are neglected. Alternatively, the same objective may be achieved by considering only data points between the largest maximum and smallest minimum of the second derivative of curve in FIG. 9. Alternative electronic circuits, methods of analysis, and variety of materials that may be employed in photoresponsive potentiometric reading devices are disclosed in U.S. patent application, "Photoresponsive Detection and Discrimination," U.S. Ser. No. 231,091, filed Aug. 11, 1988, assigned to the same assignee as this application and herein incorporated by reference.

The measured rate of change in the relationship between the alternating photocurrent amplitude and the electrolyte potential is determined by the rate of change of the electrostatic surface potential present at the electrolyte-exposed surface of the photoresponsive electrode at the X-Y coordinate of irradiation with intensity-modulated light (*Science* 240, 1182–1185, May 27, 1988). This surface potential is determined by the pH of the electrolyte exposed to the surface when a pH-sensitive surface, e.g. silicon nitride is employed and is redox potential sensitive when the surface is a noble metal, e.g. platinum or gold (see U.S. Ser. No. 231,981, 072,168, and 065,418).

A photoresponsive electrode can be influenced by the redox potential of the medium adjacent the electrode surface. Various redox systems can be employed, enzyme reactions, particularly oxidoreductases, e.g., glucose oxidase, peroxidase, uricase, NAD or NADP dependent dehydrogenases, naturally occurring electron transfer agents, e.g., ferridoxin, ferritin, cytochrome C, and cytochrome $b_2$, organic electron donors and acceptor agents, e.g., methylene blue, nitro tetrazolium, Meldola blue, phenazine methosulfate, metallocenes, e.g., ferrocenium, naphthoquinone, N,N'-dimethyl 4,4'-dipyridyl, etc., and inorganic redox agents, e.g., ferri- and ferroxyanide, chloronium ion, cuprous and cupric ammonium halide, etc.

According to the foregoing specification, the slide reading assembly has a photoresponsive electrode with a multiplicity of measurement sites, and includes both a reference and a controlling electrode, as shown in FIG. 8. Alternatively, the reference electrode may be made optional by shorting the output of operation amplifier 90 and the input of operational amplifier 92, shown in FIG. 8, and making a common connection to a single counter electrode placed in the electrolyte 84. The counter electrode may be extremely simply, namely a foil or wire of a metal such as platinum, gold, iridium, titatium, etc. which is inert to the electrolyte. In this alternative mode, the photoresponsive electrode has a multiplicity of measurement sites that includes at least one control site where no analyte is present and is thereby able to, by difference, measure the rate of potential change generated by the chemical reaction due to presence of the analyte at other sites at the surface of the photoresponsive electrode.

In operation the stepper motor 63 in FIG. 7 is engaged with the plunger stem 61 to push the pad 62 of the plunger against the porous filter membrane. A chemical reaction occurs at the surface of the photoresponsive electrode between reagent in the liquid such as an enzyme substrate with an enzyme which is part of an analyte complex. Light from an LED 47 goes through the holes 43 in the housing and is absorbed within the photoresponsive electrode 45. The chemical reaction such as the reaction of urease with urea to release ammonia and carbon dioxide causes a change in pH or redox potential of the electrolyte. This in turn affects the surface potential of the photoresponsive electrode, which is turn alters the effect of light on the photoresponsive electrode.

DNA Assay Standard Curve

Membrane: biotin-BSA coated nitrocellulose membrane (0.8µ pore side).
DNA sample: 0, 5, 10, 25, 50, 100, 150, 200 pg of single-stranded Calf thymus DNA in 0.5 ml of phosphate buffered saline buffer 50 mm $NaPO_4$, 150 NaCl, 1 mm EDTA; 0.05% sodium azide pH 7.0.
Reagent: 0.5 µg/ml Streptavidin, 1 ng/ml SSB-biotin, 250 ng/ml anti-DNA-urease, 0.1% BSA in 10 mM tris·HCl buffer, 1 mM EDTA (pH 7.4) plus 0.25% triton X-100, 0.05% sodium azide.
Assay Protocol: 500 µl of DNA sample was incubated with 1000 µl of reagent at 37° for 60 minutes. The mixture was filtered through the biotin-BSA coated membrane at a flow rate of about 100 µl/min. The membrane was then washed with 1 cc of wash buffer (10 mm $NaPO_4$, 100 mm NaCl, 0.05% Tween 20, 0.05% sodium azide, pH 6.5) at a maximum flow rate of about 6 ml/min). After washing, the slide was transferred to the slide reading assembly where the liquid contains as 100 mM urea in the wash as substrate.

| Results | |
|---|---|
| DNA (Pg/sample) | Results of Signal (µV/Sec) |
| 0 | 42.0 |
| 5 | 75.5 |
| 10 | 91.0 |
| 25 | 177.5 |
| 50 | 331 |
| 100 | 656 |
| 150 | 938 |
| 200 | 1353 |

Figure 10:
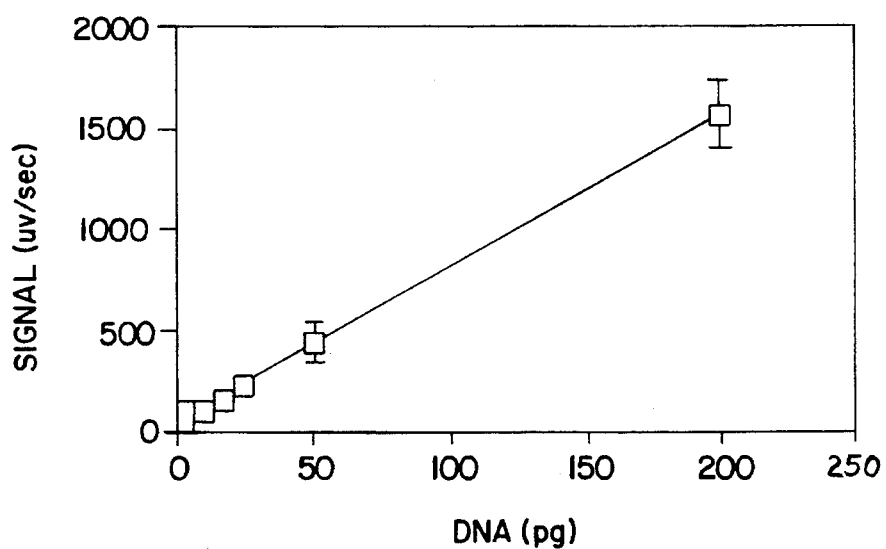
FIG. 10 Standard curve for DNA determination.
Figure 6:
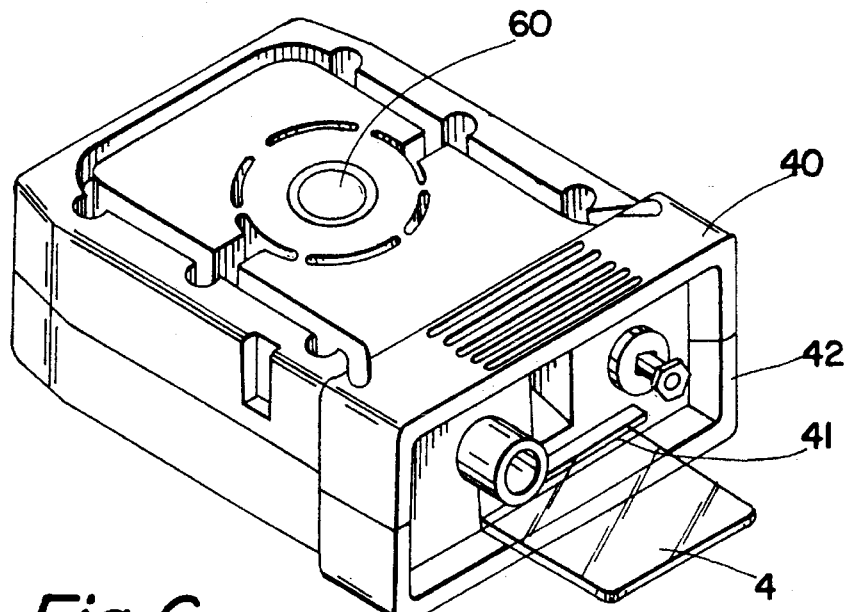
FIG. 6 Top perspective view of the slide reading assembly.
Figure 6A:
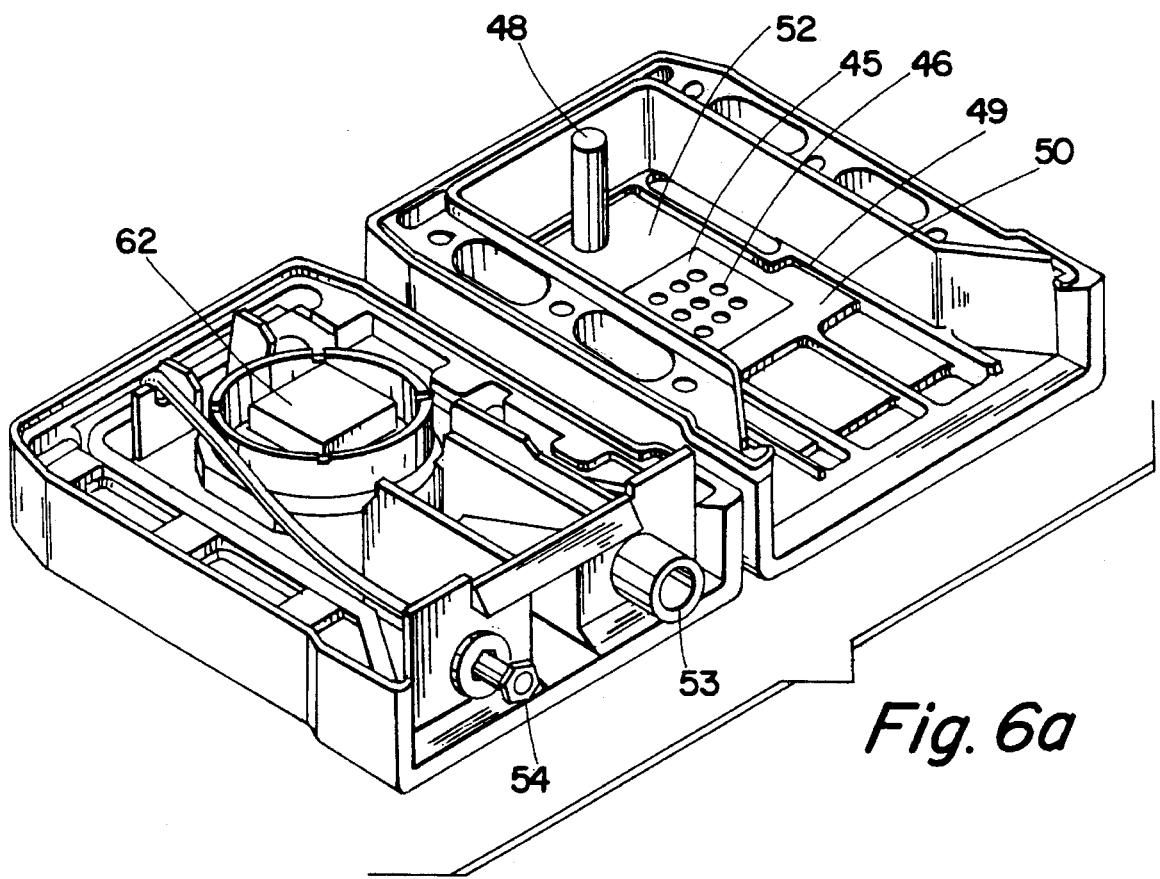
FIG. 6a Internal perspective view of the slide reading assembly.

The results are shown as a curve in FIG. 10. Thus the analytical work station permits the determination of the picogram (pg) qualities of DNA at quantities as low as 2 pg over a dynamic range of 2–200 pg.

What is claimed is:

1. A slide reading assembly comprising:

(a) a housing with a top, bottom, and inner and outer sidewall sections wherein the inner side wall section has a window with a photoresponsive electrode having an inner surface mounted above the window on the inside of the inner side wall section so that light from an external source can pass into and be absorbed within the photoresponsive electrode and said outer sidewall section has a surface;

the top section of the housing having an opening for receiving a slide to be analyzed wherein the slide has a porous filter membrane with analyte to be determined on predetermined locations on the porous filter membrane, said housing having means for aligning the predetermined locations on the porous filter membrane on the inner surface of the photoresponsive electrode opposite the window in the housing which allow light to pass to a photoresponsive electrode;

a resilient plunger mounted in the outer side wall surface of the housing opposite the photoresponsive electrode, the plunger having a stem and pad such that when the plunger stem is pushed inwardly, by an operatively associated stepping motor, into the housing the pad compresses the porous membrane against the inner surface of the photoresponsive electrode;

a liquid chamber within the housing with exit and entrance ports for liquids in the top section of the housing and wherein the inner surface of the photoresponsive electrode is within the liquid chamber and the porous filter membrane is aligned above the inner surface of the photoresponsive electrode in the liquid chamber;

(b) an intensity-modulated light source for independently irradiating the photoresponsive electrode through the window in the housing on each area of the photoresponsive electrode opposite the area of the porous filter having a predetermined location of filtered analyte or analyte complex; and (c) an electrical means for measuring a potential change of the surface of the photoresponsive electrode when the photoresponsive electrode is exposed to an intensity-modulated beam of light through the window in the housing and a chemical reaction is occurring between the filtered analyte or analyte complex on the porous filter membrane and a reagent in the liquid in the liquid chamber, the electrical means including a counter electrode, and an operation amplifier.

2. A slide reading assembly according to claim 1 wherein the inner surface of the photoresponsive electrode has a coating of insulation.

3. A slide reading assembly according to claim 1 wherein the pad of the plunger is pivotally mounted on the stem of the plunger.

4. A slide reading assembly according to claim 1 wherein the slide alignment means is a slide support member with a depression that fits the configuration of the slide and a peg that fits a notch in the slide.

5. A slide reading assembly according to claim 1 wherein the alignment means is a peg at the bottom section of the housing and a depression on a slide support member to fit the shape of the slide.

6. A slide reading assembly according to claim 1 which has a reference electrode.

7. A slide reading assembly according to claim 5, said slide comprising a thin flat generally rectangular plastic sheet with a front and rear end wherein the front end of the slide has a notch as means for aligning the slide both in a filter assembly and a reading assembly; the rear end of the slide having an area for manually grasping the slide; wherein the front, approximately a third of the slide, defines an opening which is covered with a porous filter membrane and a section of the front one third of the slide is narrower than the rear section of the slide, said narrower section also serving as a means for aligning the slide in both the filtering assembly and the reading assembly and wherein the alignment means provide for deposition of analyte complex onto predetermined locations on the porous filter membrane in the filter assembly and for detection of analyte complex at these same predetermined locations in the reading assembly.

8. A slide reading assembly according to claim 6 wherein the porous filter membrane has fixed to it a hapten and wherein the hapten is biotin.

9. A slide reading assembly according to claim 5 which has a buffering capacity of 1–10 m mole per liter of compressed membrane volume.

10. An analytical work station comprising one or more filtering assemblies and a slide reading assembly, said filtering assembly comprising in combination:

a block with a top and bottom surface, said block having a plurality of channels with inlet ports on the top surface and exit ports on the bottom surface and a first alignment means;

a vacuum plate having an inner and an outer surface wherein the outer surface has a vacuum fitting defining an area on the outer surface, with a plurality of vacuum ports from the inner to outer surface within the area defined by the vacuum fitting, said vacuum plate having a second alignment means;

a slide defining an opening which is covered by a porous filter membrane and further having a third alignment means;

wherein the block and the vacuum plate have spacing means providing space for removably inserting the slide between the block and the vacuum plate and wherein the first, second, and third alignment means align the block, vacuum plate, and slide such that the exit ports of the block, porous filter membrane, and vacuum ports are aligned so that when a vacuum is applied through the vacuum fitting, liquids in the block channels separately flow through the exit ports, through the porous filter membrane, and through the vacuum ports without liquids from one channel mixing with liquids from other channels on the porous filter membrane and wherein analyte or analyte complex in the filtered liquid are fixed on the porous filter membrane in a predetermined location, said slide reading assembly comprising:

a housing with a top, bottom and inner and outer side wall sections wherein the inner side wall section has a window with a photoresponsive electrode mounted above the window on the inside of the inner side wall section so that light from an external source can pass into and be absorbed within the photoresponsive electrode;

the top section of the housing having an opening for receiving a slide to be analyzed wherein the slide has a porous filter membrane with analyte to be determined on predetermined locations on the porous filter membrane, said housing having means for aligning the predetermined locations on the porous filter membrane on the inner surface of the photoresponsive electrode opposite the window in the housing which allow light to pass to a photoresponsive electrode;

a resilient plunger mounted in the outer side wall surface of the housing opposite the photoresponsive electrode, the plunger having a stem pad such that when the plunger stem is pushed inwardly, by an operatively associated stepping motor, into the housing the pad compresses the porous membrane against the inner surface of the photoresponsive electrode;

a liquid chamber within the housing with exit and entrance ports for liquids in the top section of the housing and wherein the inner surface of the photoresponsive electrode is within the liquid chamber and the porous filter membrane is aligned above the inner surface of the photoresponsive electrode in the liquid chamber;

an intensity-modulated light source for independently irradiating the photoresponsive electrode through the window in the housing on each area of the photoresponsive electrode opposite the area of the porous filter having a predetermined location of filtered that or that complex; and an electrical means for measuring the potential change of the surface of the photoresponsive electrode when the photoresponsive electrode is exposed to an intensity-modulated beam of light through the window in the housing and a chemical reaction is occurring between the filtered that or that complex on the porous filter membrane and a reagent in the liquid in the liquid chamber, the electrical means including a counter electrode, and an operational amplifier.

11. In combination, a filtering assembly and a slide reading assembly, said filtering assembly comprising in combination:

a block with a top and bottom surface, said block having a plurality of channels with inlet ports on the top surface and exit ports on the bottom surface and a first alignment means;

a vacuum plate having an inner and outer surface wherein the outer surface has a vacuum fitting defining an area on the outer surface, with a plurality of vacuum ports from the inner to outer surface within the area defined by the vacuum fitting, said vacuum plate having a second alignment means;

a slide having a front end and sides, the slide defining an opening which is covered by a porous filter membrane and further having a third alignment means;

wherein the block and the vacuum plate have spacing means providing space for removably inserting the slide between the block and the vacuum plate and wherein the first, second, and third alignment means align the block, vacuum plate, and slide such that the exit ports of the block, porous filter membrane, and vacuum ports are aligned so that when a vacuum is applied through the vacuum fitting, liquids in the block channels separately flow through the exit ports, through the porous filter membrane, and through the vacuum ports without liquids from one channel mixing with liquids from other channels on the porous filter membrane and wherein analyte or analyte complex in the filtered liquid filtered through the membrane are fixed on the porous filter membrane in predetermined locations, said third alignment means providing additionally for positioning the slide in the slide reading assembly so that detection will occur at the same predetermined locations on the porous membrane, and said slide reading assembly comprising a housing with a top, bottom and inner and outer side wall sections, said inner side wall section having an electrode mounted thereon, the top section of the housing having an opening for receiving the slide and the housing having a fourth alignment means for aligning the predetermined locations on the porous membrane to corresponding predetermined locations on the surface of the electrode.

12. A filter assembly according to claim 11, wherein the first alignment means is a hole in the bottom surface of the block; the second alignment means is a peg in the vacuum plate that is received by the hole; the third alignment means is a notch in the front end of the slide, which engages the peg; and the top surface of the vacuum plate has a depression that conforms to the shape of the sides of the slide.

13. In combination, one or more filtering assemblies, each comprising a block with a top and bottom surface, said block having a plurality of channels with inlet ports on the top surface and exit ports on the bottom surface and a fist alignment means;

a vacuum plate having an inner and outer surface wherein the outer surface has a vacuum fitting defining an area on the outer surface, with a plurality of vacuum ports from the inner to outer surface within the area defined by the vacuum fitting, said vacuum plate having a second alignment means;

a slide having a front end and sides, the slide defining an opening which is covered by a porous filter membrane and further having a third alignment means;

wherein the block and the vacuum plate have spacing means providing space for removably inserting the slide between the block and the vacuum plate and wherein the first, second, and third alignment means align the block, vacuum plate, and slide such that the exit ports of the block, porous filter membrane and vacuum ports are aligned so that when a vacuum is applied through the vacuum fitting, liquids in the block channels separately flow through the exit ports, through the porous filter membrane, and through the vacuum ports without liquids from one channel mixing with liquids from other channels on the porous filter membrane and wherein analyte or analyte complex in the liquid filtered through the membrane are fixed on the porous filter membrane in predetermined locations;

a slide reading assembly cooperating with the filtering assembly, said slide reading assembly comprising a housing with a top, bottom and inner and outer side walls, said inner side wall having an electrode mounted thereon, the housing including a top section having an opening for receiving the slide, said slide being positioned so that detection will occur at the same predetermined locations on the porous membrane, and said housing having a fourth alignment means for aligning the predetermined locations on the porous membrane to corresponding predetermined locations on the surface of the electrode.

14. The combination of claim 13 wherein the third alignment means provides additionally for positioning the slide in the slide reading assembly so that detection will occur at the same predetermined locations on the porous membrane.

15. In combination, a filtering assembly comprising a block with top and bottom surface, said block having a plurality of channels with inlet ports on the top surface and exit ports on the bottom surface and a first alignment means; a vacuum plate having an inner and outer surface wherein the outer surface has a vacuum fitting defining an area on the outer surface, with a plurality of vacuum ports from the inner to outer surface within the area defined by the vacuum fitting, said vacuum plate having a second alignment means; a slide having a front end and sides, the slide defining an opening which is covered by a porous filter membrane and further having a third alignment means; wherein the block and the vacuum plate have spacing means providing space for removably inserting the slide between the block and the vacuum plate and wherein the first, second, and third alignment means align the block, vacuum plate, and slide such that the exit ports are aligned so that when a vacuum is applied through the vacuum fitting, liquids in the block channels separately flow through the exit ports, through the porous filter membrane, and through the vacuum ports without liquids from one channel mixing with liquids from other channels on the porous filter membrane and wherein analyte or analyte complex in the liquid filtered through the membrane are fixed on the porous filter membrane in predetermined locations, and a slide reading assembly comprising a housing with a top, bottom, and inner and outer sidewall sections wherein the inner side wall section has a window with an electrode mounted thereon; the housing having a top section having an opening for receiving said slide to be analyzed; and wherein the third alignment means provides additionally for positioning the slide in said slide reading assembly so that detection will occur at the same predetermined locations on the porous membrane a photoresponsive electrode having an inner surface, means mounted in the outer side wall surface of the housing for compressing the porous membrane against the inner surface of the photoresponsive electrode; a liquid chamber within the housing with exit and entrance ports for liquids in the top section of the housing and wherein the inner surface of the photoresponsive electrode is within the liquid chamber and the porous membrane is aligned above the inner surface of the photoresponsive electrode in the liquid chamber a window on the housing on each side of the photoresponsive device; an intensity-modulated light source for independently irradiating the photoresponsive electrode through said window in the housing on each side of the photoresponsive electrode opposite the area of the porous membrane and an electrical means for measuring a potential change of the surface of the photoresponsive electrode when the photoresponsive electrode is exposed to an intensity-modulated beam of light through the window in the housing and a chemical reaction is occurring between the filtered analyte or analyte complex on the porous filter membrane and a reagent in the liquid in the liquid chamber.

* * * * *